US00PP31588P2

(12) United States Plant Patent
van der Arend

(10) Patent No.: US PP31,588 P2
(45) Date of Patent: Mar. 24, 2020

(54) ***MURDANNIA* PLANT NAMED 'PPIMUR004'**

(50) Latin Name: *Murdannia loriformis*
Varietal Denomination: PPIMUR004

(71) Applicant: Rene P. A. van der Arend, Naaldwijk (NL)

(72) Inventor: Rene P. A. van der Arend, Naaldwijk (NL)

(73) Assignee: Plant Planet International B.V., Naaldwijk (NL)

( * ) Notice: Subject to any disclaimer, the term of this patent is extended or adjusted under 35 U.S.C. 154(b) by 0 days.

(21) Appl. No.: 16/501,092

(22) Filed: Feb. 21, 2019

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Murdannia* plant named 'PPIMUR004', characterized by its upright to outwardly spreading plant habit; freely basal clumping growth habit; vigorous growth habit; green-colored leaves with dark greyed green-colored venation; freely flowering habit; and white-colored flowers arranged in dense inflorescences.

2 Drawing Sheets

Botanical designation: *Murdannia loriformis*.
Cultivar denomination: 'PPIMUR004'.

BACKGROUND OF THE INVENTION

The present invention relates to a new and distinct cultivar of *Murdannia* plant, botanically known as *Murdannia loriformis*, typically grown as a container *Murdannia* plant and hereinafter referred to by the name 'PPIMUR004'.

The new *Murdannia* plant is a naturally-occurring whole plant mutation of an unnamed selection of *Murdannia loriformis*, not patented. The new *Murdannia* plant was discovered and selected by the Inventor as a single plant from within a population of plants of the unnamed selection in a controlled environment in Southeast Asia on Nov. 20, 2016.

Asexual reproduction of the new *Murdannia* plant by cuttings in Naaldwijk, The Netherlands since June, 2017 has shown that the unique features of this new *Murdannia* plant are stable and reproduced true to type in successive generations of asexual reproduction.

SUMMARY OF THE INVENTION

The following traits have been repeatedly observed and are determined to be the unique characteristics of 'PPIMUR004'. These characteristics in combination distinguish 'PPIMUR004' as a new and distinct *Murdannia* plant:

1. Upright to outwardly spreading plant habit.
2. Freely basal clumping growth habit.
3. Vigorous growth habit.
4. Green-colored leaves with dark greyed green-colored venation.
5. Freely flowering habit.
6. White-colored flowers arranged in dense inflorescences.

Plants of the new *Murdannia* differ primarily from plants of the mutation parent in leaf color as plants of the mutation parent have solid green-colored leaves without discernible venation.

Plants of the new *Murdannia* can be compared to plants of unnamed selections of *Murdannia loriformis* known to the Inventor, not patented. In side-by-side comparisons conducted in Naaldwijk, The Netherlands, plants of the new *Murdannia* differ primarily from plants of unnamed selections of *Murdannia loriformis* known to the Inventor in leaf color as leaves of plants of the new *Murdannia* are green in color with dark greyed green-colored venation whereas leaves of plants of unnamed selections are solid green in color without discernible venation.

BRIEF DESCRIPTION OF THE PHOTOGRAPHS

The accompanying colored photographs illustrate the overall appearance of the new *Murdannia* plant showing the colors as true as it is reasonably possible to obtain in colored reproductions of this type. Colors in the photographs may differ slightly from the color values cited in the detailed botanical description which accurately describe the colors of the new *Murdannia* plant.

The photograph on the first sheet is a side perspective view of typical plants of 'PPIMUR004' grown in a container.

The photograph on the second sheet is a close-up view of a typical flowering stem of 'PPIMUR004'.

DETAILED BOTANICAL DESCRIPTION

The aforementioned photographs and following observations, measurements and values describe plants grown during the winter in 11-cm containers in a glass-covered greenhouse in Naaldwijk, The Netherlands and under cultural practices typical of commercial *Murdannia* production. During the production of the plants, day temperatures ranged from 10° C. to 25° C. and night temperatures ranged from 4° C. to 15° C. Plants were 17 weeks old when the photographs and the description were taken. In the following description, color references are made to The Royal Horticultural Society Colour Chart, 2015 Edition, except where general terms of ordinary dictionary significance are used.

Botanical classification: *Murdannia loriformis* 'PPIMUR004'.

Parentage: Naturally-occurring whole plant mutation of an unnamed selection of *Murdannia loriformis*, not patented.

Propagation:

*Type*.—By cuttings.

*Time to initiate roots, summer*.—About 1.5 weeks at temperatures about 22° C. to 25° C.

*Time to initiate roots, winter*.—About two weeks at temperatures about 20° C. to 22° C.

*Time to produce a rooted young plant, summer*.—About four weeks at temperatures about 22° C. to 25° C.

*Time to produce a rooted young plant, winter*.—About four weeks at temperatures about 20° C. to 22° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial; roughly flattened globular in overall shape; upright to outwardly spreading plant habit; vigorous growth habit.

*Plant height, soil level to top of foliar plane*.—About 10.2 cm.

*Plant height, soil level to top of floral plane*.—About 21.6 cm.

*Plant diameter or spread*.—About 29.1 cm.

Branch description:

*Branching habit*.—Freely branching habit with about seven primary branches per plant each primary branch with about four secondary lateral branches.

*Length*.—About 6.2 cm.

*Diameter*.—About 4.5 mm.

*Internode length*.—About 1.3 cm.

*Strength*.—Moderately strong.

*Aspect*.—About 90° from vertical.

*Texture and luster*.—Smooth, glabrous; moderately glossy.

*Color*.—Close to between 145D and 157A; at the internodes, close to 137B and 144C; with development, color becoming closer to 144C.

Leaf description:

*Arrangement*.—Distichous, simple and sessile.

*Length*.—About 9.8 cm.

*Width*.—About 3.3 cm.

*Shape*.—Narrowly ovate to narrowly elliptic.

*Apex*.—Apiculate to acuminate.

*Base*.—Cuneate, sheathing.

*Margin*.—Entire; moderately undulate.

*Texture and luster, upper surface*.—Smooth, glabrous; slightly velvety; slightly glossy.

*Texture and luster, lower surface*.—Smooth, glabrous; moderately velvety; slightly glossy.

*Venation pattern*.—Parallel.

*Color*.—Developing leaves, upper surface: Close to 191A to 191C; towards the margins, close to 143A. Developing leaves, lower surface: Close to 138B tinged with close to 194B. Fully expanded leaves, upper surface: Close to NN137A; venation, close to between 189A and 190A; marginal venation, close to NN137A. Fully expanded leaves, lower surface: Close to 191A to 191B; venation, close to 147B.

*Leaf sheaths*.—Length: About 1.6 cm. Width: About 6 mm. Texture and luster, upper surface: Smooth, glabrous; moderately glossy. Texture and luster, lower surface: Smooth, glabrous; matte. Color, upper surface: Close to 147D. Color, lower surface: Close to 145B to 145C; venation, close to 143A.

Flower description:

*Flower type and flowering habit*.—Single flowers arranged in terminal panicle; flowers face mostly upright to slightly outwardly; freely flowering habit, each panicle with about 65 flowers and about 700 flowers developing per plant over the flowering season.

*Fragrance*.—None detected.

*Time of flowering*.—In The Netherlands, plants flower continuously from autumn into the spring.

*Flower longevity*.—Individual flowers last about ten days on the plant; flowers persistent.

*Inflorescence length*.—About 16.3 cm.

*Inflorescence width*.—About 8.8 cm.

*Flower diameter*.—About 6 mm by 9 mm.

*Flower depth* (*height*).—About 7 mm.

*Flower buds*.—Height: About 2.5 mm. Diameter: About 1.5 mm. Shape: Obovate. Texture and luster: Smooth, glabrous; glossy. Color: Close to 144B; towards the apex, close to 147A.

*Petals*.—Quantity and arrangement: About three arranged in a single whorl. Length: About 4 mm. Width: About 2 mm. Shape: Obovate. Apex: Obtuse. Base: Cuneate. Margin: Entire; not undulate. Texture and luster, upper surface: Smooth, glabrous; slightly velvety; matte. Texture and luster, lower surface: Smooth, glabrous; matte. Color: When opening, upper and lower surfaces: Close to NN155D. Fully opened, upper and lower surfaces: Close to NN155D; color does not change with development.

*Sepals*.—Quantity and arrangement: About three sepals arranged in a single whorl. Length: About 3 mm. Width: About 2 mm. Shape: Ovate. Apex: Broadly and bluntly acute. Base: Cuneate. Margin: Entire. Texture and luster, upper and lower surfaces: Smooth, glabrous; slightly glossy. Color: When opening, upper and lower surfaces: Close to 157D; towards the apex, close to 147B to 147D. Fully opened, upper and lower surfaces: Close to NN157B; towards the apex, close to 147C to 147D.

*Peduncles*.—Length: About 14.7 cm. Diameter: About 1.5 mm. Strength: Moderately strong; flexible. Aspect: About 25° from lateral branch. Texture and luster: Moderately to densely pubescent; moderately glossy. Color: Close to 143A to 143B.

*Pedicels*.—Length: About 4 mm. Diameter: About 0.5 mm. Strength: Moderately strong; flexible. Aspect: About 45° from peduncle axis. Texture and luster: Smooth, glabrous; slightly glossy. Color: Close to 145C.

*Reproductive organs*.—Stamens: Quantity: Six per flower; three functional anthers and three non-functional anthers. Filament length, functional anthers: About 1.5 mm. Filament length, non-functional anthers: About 0.75 mm. Filament color, functional and non-functional anthers: Close to NN155D. Anther shape, functional anthers: Narrowly oblong. Anther shape, non-functional anthers: Three-lobed. Anther size, functional anthers: About 1 mm by 0.5 mm. Anther size, non-functional anthers: About 0.7 mm by 0.4 mm. Anther color, functional anthers: Close to 156D. Anther color, non-functional anthers: Close to 6B. Pollen amount, functional anthers: Scarce. Pollen color, functional anthers: Close to 11D. Pollen amount, non-functional anthers: None observed. Pistils: Quantity: One per flower. Pistil length: About 2.5 mm. Style length: About 2.3 mm. Style color: Close to 155C. Stigma diameter: About 0.2 mm. Stigma shape: Lanceolate, pointed. Stigma color: Close to 155C. Ovary color: Close to 155C.

*Seeds and fruits*.—To date, seed and fruit development has not been observed on plants of the new *Murdannia*.

Pathogen & pest resistance: To date, resistance to pathogens and pests common to *Murdannia* plants has not been observed on plants of the new *Murdannia* grown under commercial production conditions.

Garden performance: Plants of the new *Murdannia* have been observed to tolerate rain, wind and temperatures ranging from 5° C. to 40° C.; plants of the new *Murdannia* and are suitable for USDA Hardiness Zones 10 to 13.

It is claimed:

1. A new and distinct *Murdannia* plant named 'PPIMUR004' as illustrated and described.

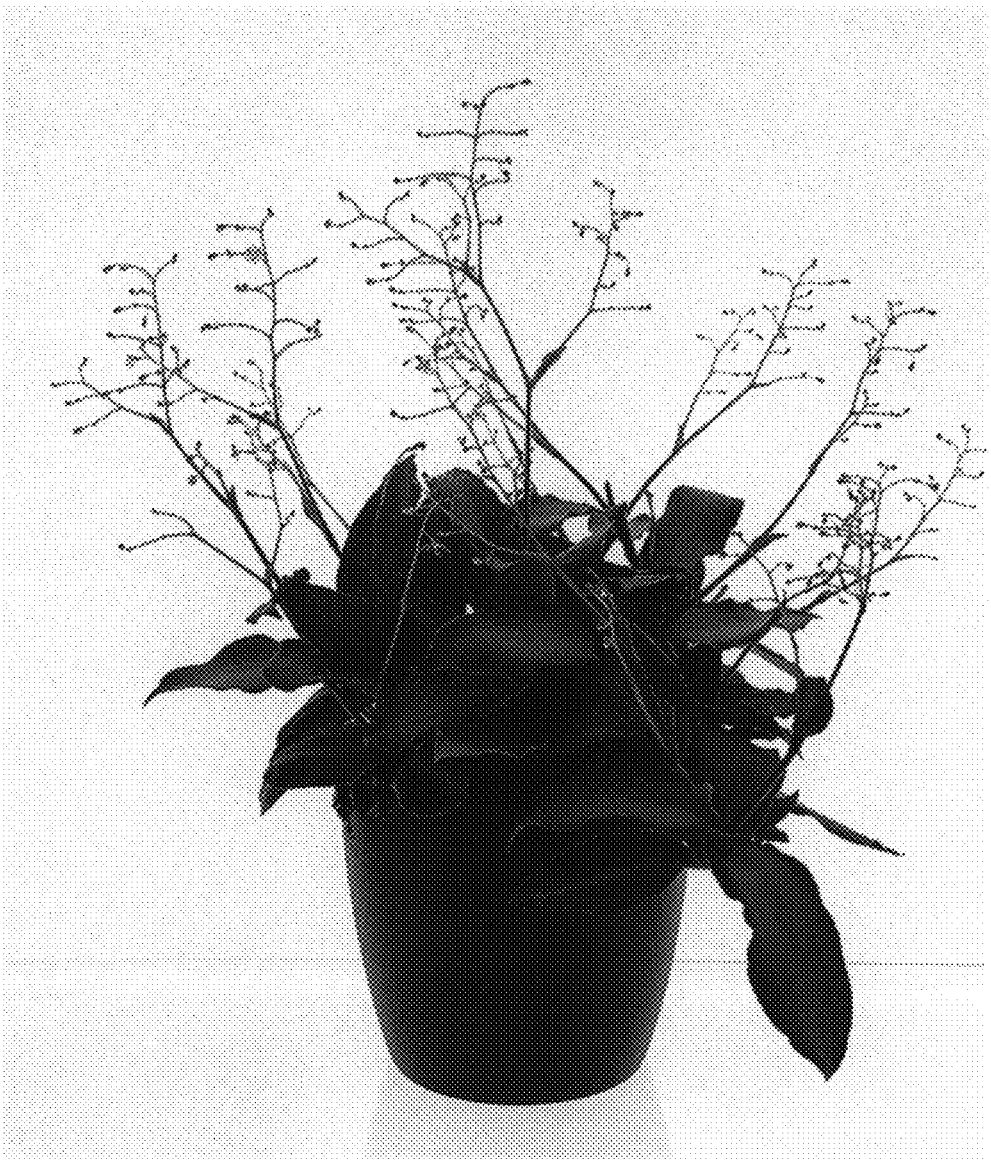

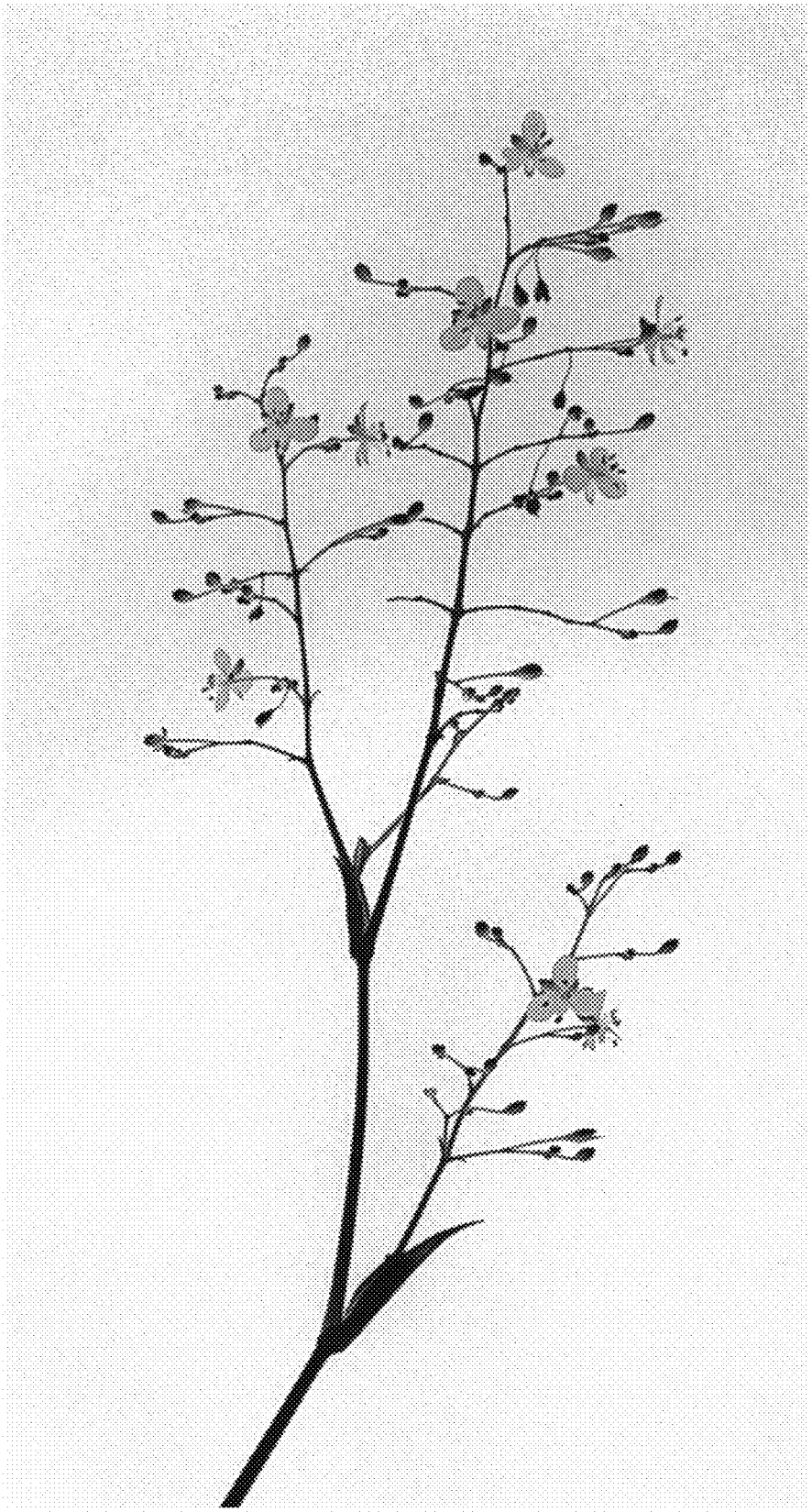

* * * * *